United States Patent [19]

Sundeen et al.

[11] Patent Number: 4,536,501

[45] Date of Patent: Aug. 20, 1985

[54] SUBSTITUTED 4-PHENOXY OR 4-PHENYLTHIO PROLINES

[75] Inventors: Joseph E. Sundeen, Yardley, Pa.; Rudiger D. Haugwitz, Titusville; Peter W. Sprague, Pennington, both of N.J.

[73] Assignee: E. R. Squibb & Sons, Inc., Princeton, N.J.

[21] Appl. No.: 595,219

[22] Filed: Mar. 30, 1984

[51] Int. Cl.³ .................. C07D 417/12; A61K 31/54
[52] U.S. Cl. ........................... 514/225; 514/80; 544/12; 544/13
[58] Field of Search ................ 424/200, 246; 544/12, 544/13; 514/225, 80

[56] References Cited

U.S. PATENT DOCUMENTS

| | | | |
|---|---|---|---|
| 4,105,776 | 8/1978 | Ondetti et al. | 424/274 |
| 4,168,267 | 9/1979 | Petrillo | 260/326.2 |
| 4,217,347 | 8/1980 | Horovitz et al. | 424/246 |
| 4,316,906 | 2/1982 | Ondetti et al. | 424/274 |
| 4,337,201 | 6/1982 | Petrillo | 548/413 |
| 4,374,829 | 2/1983 | Harris et al. | 424/177 |
| 4,431,644 | 2/1984 | Smith et al. | 424/246 |
| 4,431,645 | 2/1984 | Smith et al. | 424/246 |

FOREIGN PATENT DOCUMENTS

| | | |
|---|---|---|
| 13837 | 11/1983 | Australia . |
| 879158 | 2/1980 | Belgium . |
| 18549 | 11/1980 | European Pat. Off. . |
| 88350 | 9/1983 | European Pat. Off. . |
| 95584 | 12/1983 | European Pat. Off. ............... 544/12 |
| 5151555 | 11/1980 | Japan . |

*Primary Examiner*—John M. Ford
*Attorney, Agent, or Firm*—Lawrence S. Levinson; Stephen B. Davis

[57] ABSTRACT

Compounds of the formula

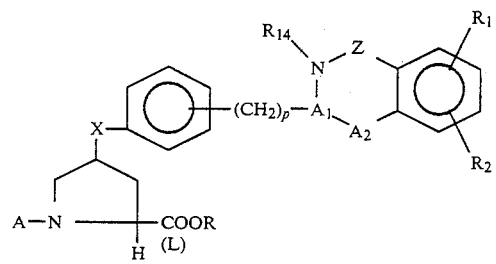

are disclosed. They possess angiotensin converting enzyme inhibition activity and diuretic activity and are therefore useful as antihypertensive agents.

21 Claims, No Drawings

SUBSTITUTED 4-PHENOXY OR 4-PHENYLTHIO PROLINES

BACKGROUND OF THE INVENTION

Haugwitz et al. in European Patent Application No. 95,584A disclose various N-substituted prolines having a diuretic moiety coupled directly to a 4-phenylthio or 4-phenoxy substituent on the proline ring.

Ondetti et al. in U.S. Pat. No. 4,105,776 disclose that various mercaptoacyl derivatives of proline, hydroxy substituted proline, and alkyl substituted proline are useful hypotensive agents due to their angiotensin converting enzyme inhibition activity.

Ondetti et al. in U.S. Pat. No. 4,316,906 disclose that mercaptoacyl derivatives of various ether and thioether substituted prolines are also useful hypotensive agents due to their angiotensin converting enzyme inhibition activity.

Horovitz et al. in U.S. Pat. No. 4,217,347 disclose reducing blood pressure by administering a composition including a diuretic and the mercaptoacyl proline compounds taught by Ondetti et al. in U.S. Pat. No. 4,105,776.

Yoshitomi in Belgian Pat. No. 879,158 disclose chlorosulfamoylbenzoylthiopropionyl prolines and thiazolidines as possessing diuretic and hypotensive activity.

Tanabe in European Patent Application No. 18,549 disclose angiotensin converting enzyme inhibitors having a carboxyethylcarbamoyl group attached to the N-atom of tetrahydroisoquinoline carboxylic acid and this same sidechain coupled to the N-atom of proline is disclosed in Japanese Application No. 5151-555.

Harris et al. in U.S. Pat. No. 4,374,829 disclose that various carboxyalkyl dipeptides are angiotensin converting enzyme inhibitors.

Petrillo in U.S. Pat. Nos. 4,168,267 and 4,337,201 disclose that various phosphinylalkanoyl prolines, substituted prolines, and their esters are angiotensin converting enzyme inhibitors.

SUMMARY OF THE INVENTION

This invention relates to new substituted 4-phenoxy or 4-phenylthio prolines and salts thereof of the formula $$\text{(I)}$$

wherein
p is one, two, three or four.
X is oxygen or sulfur.
—$A_1$—$A_2$— is —CH—NH— or —C═N—.

A is $R_4$—S—CH$_2$—CH(R$_3$)—C(O)—, $R_8$OOC—(CH$_2$)$_2$—N(R$_7$)—C(O)—,

-continued
$R_9$OOC—CH(R$_{10}$)—NH(R$_{11}$)—C(O)—, or $R_{12}$—P(O)(OR$_{13}$)—CH$_2$—C(O)—.

R, $R_8$ and $R_9$ are independently selected from hydrogen, lower alkyl, benzyl, benzhydryl, and salt forming ion.

$R_1$ and $R_2$ are independently selected from hydrogen, halogen, lower alkyl, lower alkoxy, halo substituted lower alkyl, nitro, and —SO$_2$NH$_2$.

Z is $$-\overset{O}{\underset{\|}{C}}- \quad \text{or} \quad -\overset{O}{\underset{\|}{\overset{\|}{S}}}-$$

$R_3$ is hydrogen, lower alkyl, halo substituted lower alkyl, phenyl, benzyl, phenethyl or cycloalkyl.
$R_4$ is hydrogen or $$R_5-\overset{O}{\underset{\|}{C}}-.$$

$R_5$ is lower alkyl, (phenyl with $R_6$)—(CH$_2$)$_n$—, (thienyl)—(CH$_2$)$_n$—, (furyl)—(CH$_2$)$_n$— or (pyridyl)—(CH$_2$)$_n$—.

n is zero, one, two, three or four.
$R_6$ is hydrogen, lower alkyl, lower alkoxy, halogen, or hydroxy
$R_7$ is lower alkyl or cycloalkyl.
$R_{10}$ is hydrogen, lower alkyl, (phenyl with $R_6$)—(CH$_2$)$_n$—, halo substituted lower alkyl, hydroxy substituted lower alkyl, —(CH$_2$)$_q$-cycloalkyl, —(CH$_2$)$_q$-N(lower alkyl)$_2$, —(CH$_2$)$_q$—NH$_2$, —(CH$_2$)$_q$-carboxy, —(CH$_2$)$_q$—SH, —(CH$_2$)$_q$-S-lower alkyl, —(CH$_2$)$_q$—(phenyl)—OH with OH, —(CH$_2$)$_q$—(indolyl), —(CH$_2$)$_q$—(imidazolyl), -continued

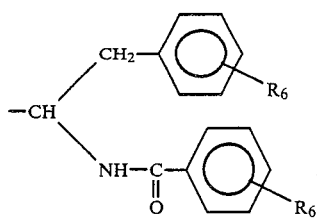

q is one, two, three or four.

$R_{11}$ is hydrogen, lower alkyl, halo substituted lower alkyl, hydroxy substituted lower alkyl, —(CH$_2$)$_q$—NH$_2$, —(CH$_2$)$_q$-N(lower alkyl)$_2$, —(CH$_2$)$_q$-guanidinyl,

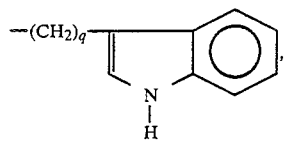

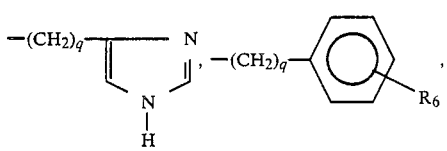

—(CH$_2$)$_q$—C(=O)—NH$_2$, —CH$_2$—S—(CH$_2$)$_2$—NH$_2$,

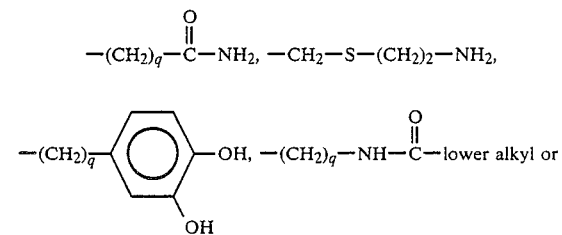

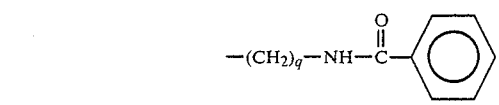

$R_{12}$ is alkyl of 1 to 10 carbons,

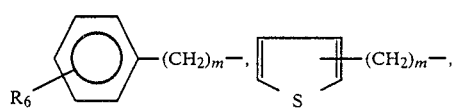

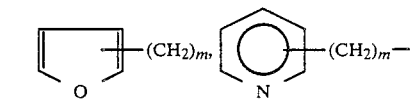

or cycloalkyl-(CH$_2$)$_m$—.
m is zero or an integer from 1 to 7.
$R_{13}$ is hydrogen, lower alkyl, benzyl, benzhydryl, salt forming ion or

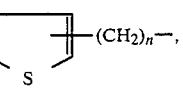

$R_{15}$ is hydrogen, lower alkyl, cycloalkyl or phenyl.
$R_{16}$ is hydrogen, lower alkyl, lower alkoxy, cycloalkyl, phenyl, benzyl, or phenethyl.
$R_{14}$ is hydrogen, lower alkyl, cycloalkyl-(CH$_2$)$_n$—,

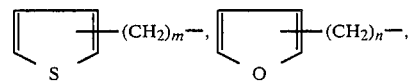

halo substituted lower alkyl, hydroxy substituted lower alkyl, —(CH$_2$)$_q$-N(lower alkyl)$_2$, or —(CH$_2$)$_q$—NH$_2$.
The symbols

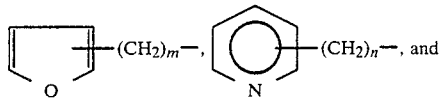

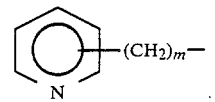

represent that the alkylene bridge is attached to an available carbon atom.

DETAILED DESCRIPTION OF THE INVENTION

This invention in its broadest aspects relates to the substituted 4-phenoxy and 4-phenylthio prolines of formula I above, to various intermediates for these compounds, to compositions containing such compounds and to the method of using such compounds as hypotensive agents.

The term lower alkyl as used in defining various symbols are straight or branched chain hydrocarbon radicals having up to seven carbons, for example, methyl, ethyl, propyl, isopropyl, butyl, t-butyl, pentyl, etc. The preferred lower alkyl groups are up to four carbons with methyl and ethyl being most preferred. Similarly, the term lower alkoxy refers to such lower alkyl groups attached to an oxygen.

The term halogen refers to chloro, bromo, and fluoro. The term halo substituted lower alkyl refers to such lower alkyl groups described above in which one or more hydrogens have been replaced by chloro, bromo, or fluoro groups such as trifluoromethyl, which is preferred, 2,2,2-trichloroethyl, chloromethyl, bromomethyl, etc. Similarly, the term hydroxy substituted lower alkyl refers to such lower alkyl groups in which one or more hydrogens have been replaced by hydroxy such as hydroxymethyl, 2-hydroxyethyl, etc.

The term cycloalkyl refers to saturated rings of 3 to 7 carbons with cyclopentyl and cyclohexyl being preferred.

The compounds of formula I wherein A is

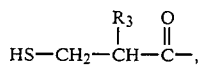

$A_1$-$A_2$ is —CH—NH—, and R is hydrogen are prepared by treating a compound of the formula

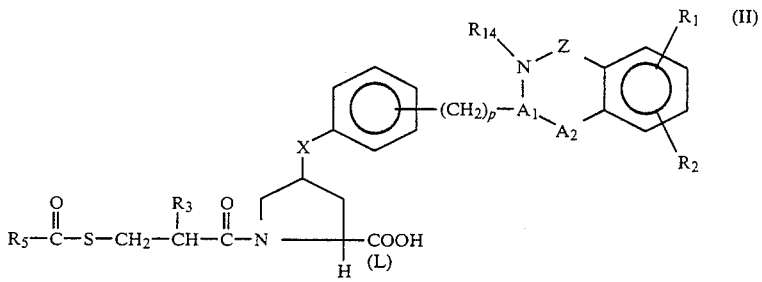

with base such as sodium hydroxide.

The compounds of formula II wherein $A_1$-$A_2$ is —CH—NH— are prepared by reacting a substituted phenoxy or phenylthio proline ester of the formula

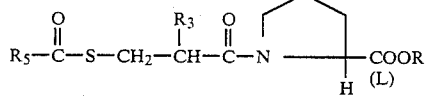

wherein Y is —CH=CH—OCH₃ when p is one and Y is

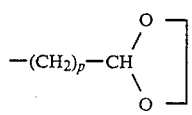

when p is two, three or four and R is an acid cleavable ester group such as benzhydryl with a substituted benzenamine of the formula

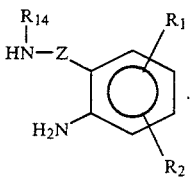

Removal of the R ester group yields the compounds of formula II. The intermediates of formula III are obtained by treating the 4-hydroxy substituted proline esters of the formula

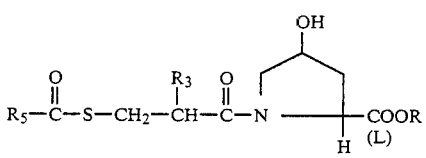

with the substituted phenol or thiophenol of the formula

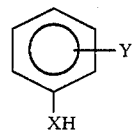

in the presence of triphenylphosphine and dialkylazodicarboxylate.

The compounds of formula I wherein A is

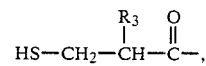

$A_1$-$A_2$ is —C=N—, and R is hydrogen are prepared by treating a compound of the formula

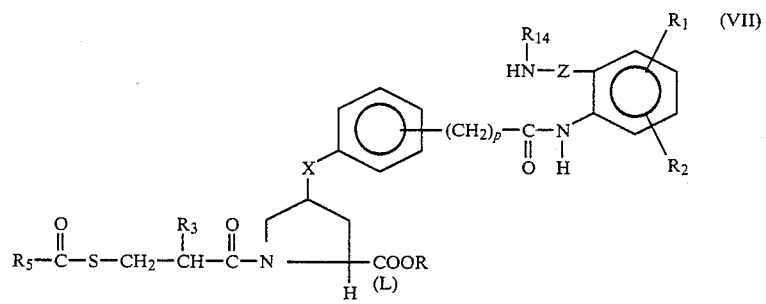

with a concentrated aqueous solution of ammonia, i.e., ammonium hydroxide, followed by treatment with sodium hydroxide to remove the methyl ester group.

The intermediates of formula VII are prepared by reacting a substituted phenoxy or phenylthio proline ester of the formula

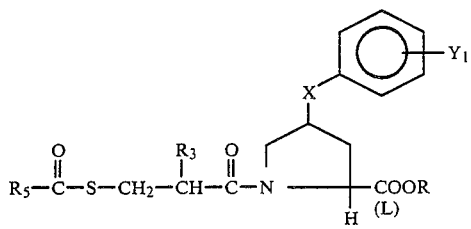

wherein $Y_1$ is

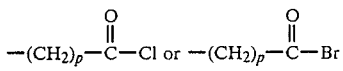

with a substituted benzenamine of formula IV in a refluxing solvent such as dioxane. The compounds of formula VIII are prepared by treating the corresponding compound wherein $Y_1$ is $-(CH_2)_p-COOH$ with an agent such as thionyl chloride or phosphorus tribromide in a solvent such as dichloromethane and with a catalyst such as dimethylformamide.

The compounds of formula I wherein A is

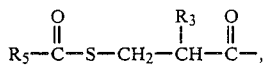

$A_1-A_2$ is $-C=N-$, and R is hydrogen are prepared by treating the corresponding compound wherein A is

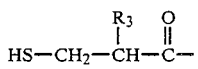

with an acid

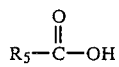

in the presence of a suitable activating agent such as dicyclohexylcarbodiimide or with an activated derivative such as

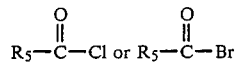

in the presence of a suitable acid acceptor such as pyridine or triethylamine.

The compounds of formula I wherein A is

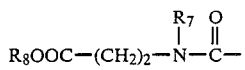

and $A_1-A_2$ is $-CH-NH-$ are prepared by reacting a 4-hydroxy proline benzyl ester with an alkylaminopropanoate of the formula

wherein $R_8$ is lower alkyl in the presence of phosgene and N-methylmorpholine to yield the substituted 4-hydroxy proline benzyl ester of the formula

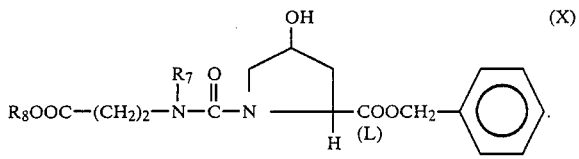

Treatment of the product of formula X with the substituted phenol or thiophenol of formula VI in the presence of triphenylphosphine and dialkylazodicarboxylate yields the intermediate of the formula

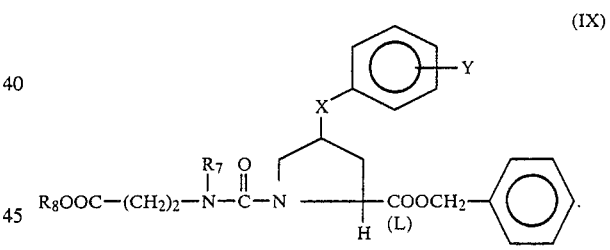

The intermediate of formula XI is then reacted with the substituted benzenamine of formula IV to yield the proline benzyl ester

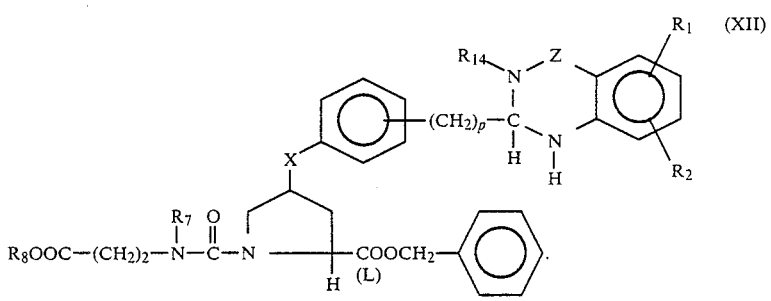

Hydrogenation of benzyl ester XII with palladium/carbon removes the benzyl ester group and yields the products of formula I wherein $R_8$ is alkyl and R is hydrogen. Further treatment with aqueous sodium hydroxide yields the diacid product of formula I, i.e., both $R_8$ and R are hydrogen.

The compounds of formula I wherein A is

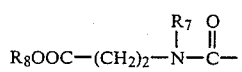

and $A_1$-$A_2$ is —C≡N— are prepared by reacting the benzyl ester of the formula

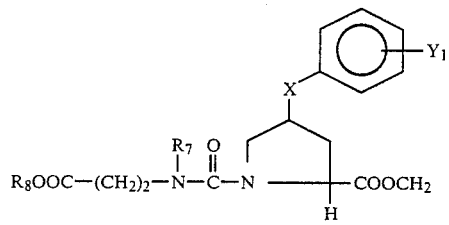

(XIII)

wherein $Y_1$ is

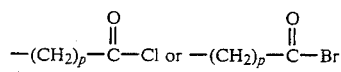

with the substituted benzenamine of formula IV to give the compound of the formula

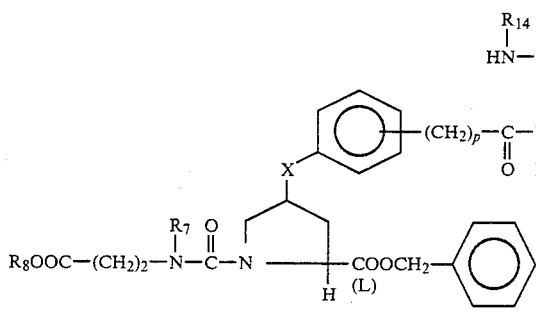

(XIV)

The compound of formula XIV is cyclized by treatment with a concentrated aqueous solution of ammonia to give the compound of the formula

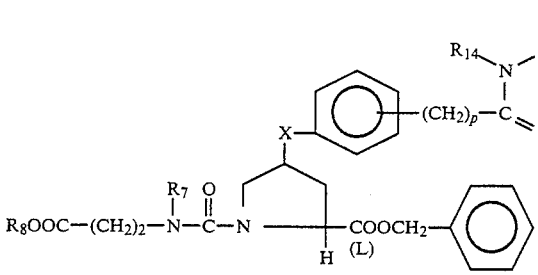

(XV)

Hydrogenation of benzyl ester XV with palladium/carbon removes the benzyl ester group and yields the products of formula I wherein $R_8$ is alkyl and R is hydrogen. Further treatment with aqueous sodium hydroxide yields the diacid product of formula I, i.e., both $R_8$ and R are hydrogen.

The compounds of formula I wherein A is

can be prepared by reacting an intermediate of the formula

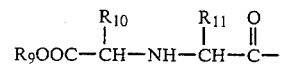

(XVI)

with the hydrochloride salt of the functionalized proline ester of the formula

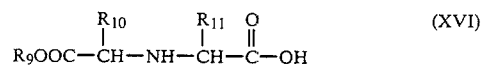

(XVII)

in the presence of triethylamine to give the compound of the formula

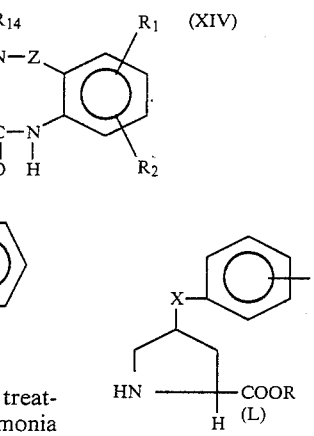

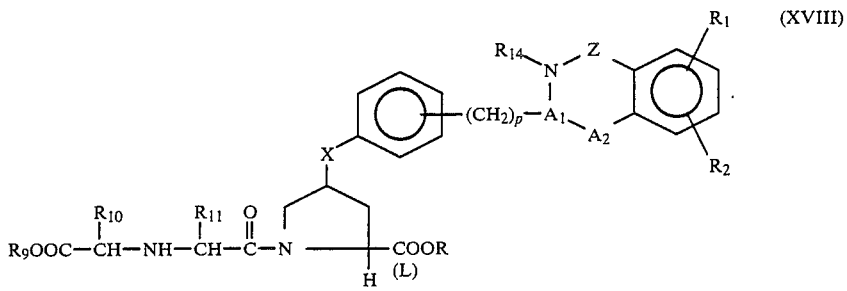

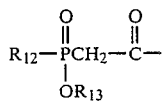

In the above reactions, the N-atom of the acid of formula XVI can be protected during the coupling step, for example, by a t-butyloxycarbonyl group.

In these procedures when $R_9$ and R are carboxy ester protecting group such as lower alkyl, benzyl or the like, they can be converted by known methods such as hydrolysis or hydrogenation to the products wherein R and/or $R_9$ are hydrogen. Reductive cleavage of the diester product wherein R is benzyl and $R_9$ is lower alkyl yields the monoester product wherein R is hydrogen and $R_9$ is lower alkyl. Similarly, reductive cleavage of the diester product wherein R is lower alkyl and $R_9$ is benzyl yields the monoester product wherein R is lower alkyl and $R_9$ is hydrogen.

The compounds of formula I wherein A is

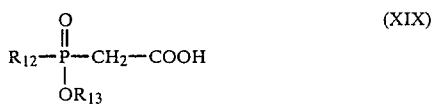

can be prepared by reacting a phosphinylacetic acid of the formula

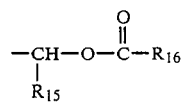

wherein $R_{13}$ is lower alkyl, benzyl or benzhydryl, with the functionalized proline ester of formula XVII. The reaction can be accomplished using known amide bond forming procedures. For example, the reaction can be run in the presence of a coupling agent such as 1,1'-carbonyldiimidazole or the acid of formula XIX can be activated by formation of its mixed anhydride, symmetrical anhydride, acid halide, acid ester, etc.

The products of formula I wherein either or both of $R_{13}$ and R are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_{13}$ and R are hydrogen.

The ester products of formula I wherein $R_{13}$ is

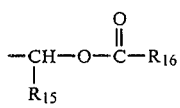

can be obtained by treating the product of formula I wherein $R_{13}$ is hydrogen or an alkali metal salt and R is benzyl or benzhydryl with the compound of the formula

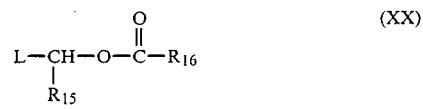

wherein L is a leaving group such as chlorine, bromine, tolylsulfonyloxy, etc., in the presence of base. Removal of the R ester group such as by hydrogenation yields the products of formula I wherein $R_{13}$ is

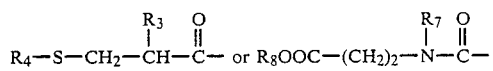

and R is hydrogen.

Of course, the products of formula I wherein A is

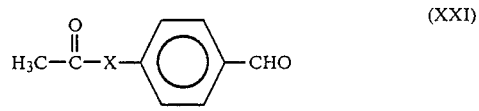

can also be prepared by coupling the appropriate sidechain with the functionalized proline ester of formula XVII.

The starting materials of formula V are disclosed by Ondetti et al. in U.S. Pat. Nos. 4,105,776 and 4,316,906. The alkylaminopropanoates of formula XI are described in the Tanabe patent applications noted above. The starting materials of formula XVI are described by Harris et al. in U.S. Pat. No. 4,374,829. The phosphinylacetic acid starting materials of formula XIX are described by Petrillo in U.S. Pat. Nos. 4,168,267 and 4,337,201.

The substituted benzenamines of formula IV are described in the literature as note, for example, Cohen et al., JACS, Vol. 82, p. 273(1960), Shetty et al., J.Med.-Chem.Vol.13, p.886 (1970), and Close et al., JACS, Vol. 82, p. 1132 (1960).

The substituted phenol or thiophenol of formula VI wherein Y is $-CH=CH-OCH_3$ are prepared by treating a benzaldehyde of the formula $$H_3C-\overset{O}{\underset{\|}{C}}-X-\!\!\left\langle\!\!\bigcirc\!\!\right\rangle\!\!-CHO \qquad (XXI)$$

with (methoxymethyl)triphenylphosphonium chloride followed by treatment with base such as sodium hydride.

The substituted phenol or thiophenol of formula VI wherein Y is

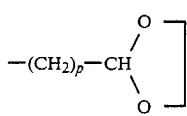

and p is two, three or four are prepared by treating a benzaldehyde of formula XXI with a triphenyl compound of the formula

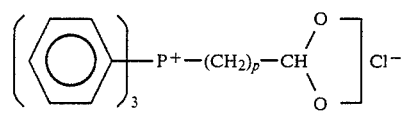

followed by hydrogenation, in the presence of, for example, palladium on carbon catalyst.

The functionalized proline ester of formula XVII wherein $A_1-A_2$ is —CH—NH— can be prepared by reacting an N-protected proline compound of the formula

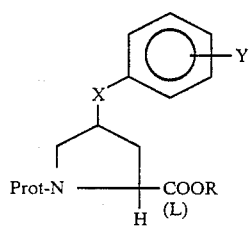

wherein Prot is a protecting group such as t-butoxycarbonyl and Y is —CH=CH—OCH$_3$ when p is one and Y is

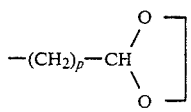

when p is two, three, or four with the substituted benzenamine of formula IV in the presence of an acid such as toluenesulfonic acid and in a solvent such as acetonitrile.

The compound of formula XXIII can be prepared by reacting the 4-hydroxy-N-protected proline ester with the substituted phenol or thiophenol of formula VI in the presence of triphenylphosphine and dialkylazodicarboxylate.

The functionalized proline ester of formula XVII wherein $A_1-A_2$ is —C=N— can be prepared by reacting an N-protected proline compound of the formula

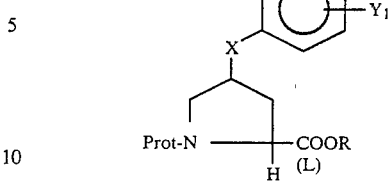

wherein Prot is a protecting group such as t-butoxycarbonyl and $Y_1$ is

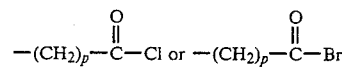

with the substituted benzenamine of formula IV in a refluxing solvent such as dioxane.

The compounds of formula XXIV are prepared from the corresponding compounds wherein $Y_1$ is —(CH$_2$)$_p$—COOH by reacting with a reagent such as oxalyl chloride or phosphorus tribromide in the presence of a catalyst dimethylformamide in a solvent such as dichloromethane.

In the above reactions if any or all of $R_{10}$, $R_{11}$ and $R_{14}$ are amino or hydroxy substituted lower alkyl,

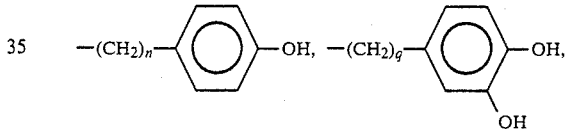

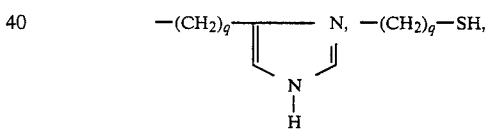

or —(CH$_2$)$_q$-guanidinyl then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known means following completion of the reaction.

Preferred compounds of this invention are those of formula I
wherein
X is oxygen.

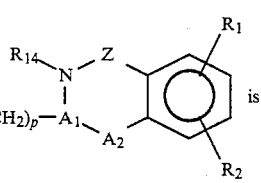

is

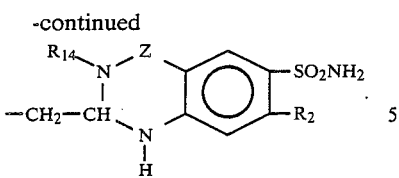

R is hydrogen, lower alkyl of 1 to 4 carbons, or an alkali metal salt ion.

$R_{14}$ is hydrogen or lower alkyl of 1 to 4 carbons, especially hydrogen or methyl.

$R_2$ is halogen, lower alkyl of 1 to 4 carbons, or halo substituted lower alkyl of 1 to 4 carbons, especially chloro or trifluoromethyl.

$R_4$ is hydrogen or

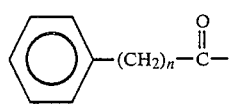

wherein n is zero, one, or two, especially hydrogen or

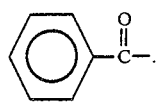

$R_3$ is lower alkyl of 1 to 4 carbons, especially methyl.

$R_8$ is hydrogen, lower alkyl of 1 to 4 carbons, or an alkali metal salt ion, especially hydrogen, ethyl, or an alkali metal salt ion.

$R_7$ is lower alkyl of 1 to 4 carbons, especially ethyl.

$R_9$ is hydrogen, lower alkyl of 1 to 4 carbons, or an alkali metal salt ion, especially hydrogen, ethyl, or an alkali metal salt ion.

$R_{10}$ is

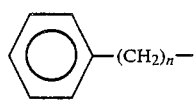

wherein n is zero, one, two, three or four, especially

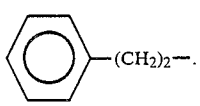

$R_{11}$ is lower alkyl of 1 to 4 carbons, $-CH_2-S-(CH_2)_2-NH_2$, or $-(CH_2)_4-NH_2$, especially methyl.

$R_{12}$ is alkyl of 1 to 10 carbons or

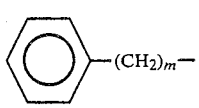

wherein m is zero or an integer from 1 to 7, especially

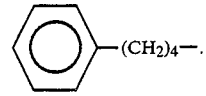

$R_{13}$ is hydrogen, alkali metal salt ion, or

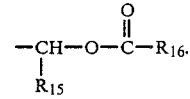

$R_{15}$ is hydrogen, straight or branched chain lower alkyl of 1 to 4 carbons, or cyclohexyl.

$R_{16}$ is straight or branched chain lower alkyl of 1 to 4 carbons.

Especially preferred are the above compounds wherein

A is

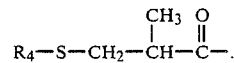

$R_4$ is hydrogen or

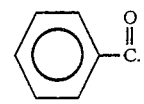

R is hydrogen.

Z is $SO_2$.

The compounds of formula I give rise to cis-trans isomerism at the 4-position of the proline ring. The configuration of the final product depends upon the configuration of the 4-hydroxy proline starting material. When the hydroxy group is in the trans-configuration, the substituted phenol or phenylthio intermediate is obtained in the cis-configuration and this configuration is maintained throughout the remainder of the reaction sequence. Similarly, if a cis-hydroxy starting material is employed the final product will be obtained in the trans configuration.

The compounds wherein A is

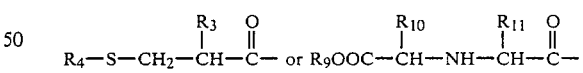

and $R_3$, $R_{10}$ and $R_{11}$ are other than hydrogen contain one or more additional asymmetric centers. These products of formula I can accordingly exist in stereoisomeric forms or as racemic mixtures thereof. The synthesis described above can utilize the racemate or one of the enantiomers as starting materials. When the racemic starting material is used in the synthetic procedure, the stereoisomers obtained in the final product can be separated by chromatographic techniques such as Pirkel or flash chromatography or fractional crystallization methods.

Preferably, if there is an asymmetric center in the sidechain it is in the S-configuration.

The compounds of this invention wherein at least one of R, $R_8$, $R_9$ and $R_{13}$ is hydrogen, form salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. The compounds of formula I also possess diuretic activity. Thus, by the administration of a composition containing one or a combination of the compounds of the invention, hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene divinylbenzene sulfonic acid cation exchange resin. HP-20 refers to a porous crosslinked polystyrene-divinyl benzene polymer resin.

EXAMPLE 1

(S)-4-[4-[[7-(Aminosulfonyl)-6-chloro-3,4-dihydro-1,1-dioxo-2H-1,2,4-benzothiadiazin-3-yl]methyl]phenoxy]-1-[(S)-3-(benzoylthio)-2-methyl-1-oxopropyl]-L-proline (a) 4-(2-Methoxyethenyl)phenol A slurry of 4-hydroxybenzaldehyde (10 g., 0.08 mole) in 125 ml. of acetic anhydride is treated with 1 ml. of pyridine (solid dissolves) and stirred at 25° for 12 hours. Evaporation in vacuo gives an oil. Water is added, and after 30 minutes the product is extracted into ethyl acetate. The organic layer is shaken sequentially with sodium bicarbonate, 10% potassium bisulfate and brine, and dried ($Na_2SO_4$). Evaporation of the dried solution gives an oil; TLC (ethyl ether/silica) shows 2 spots. This oil is filtered through a silica column with 4:1 hexane:ether to remove the more polar spot. Evaporation gives 9.9 g. of 4-acetyloxybenzaldehyde as a colorless oil; TLC (ethyl ether/silica) $R_f=0.6$.

A slurry of 31.4 g. (0.09 mole) of (methoxy-methyl)-triphenylphosphonium chloride (dried over $P_2O_5$ at 100° in vacuo for one hour) in 150 ml. of dry tetrahydrofuran is treated with 13 ml. of distilled diisopropylamine and cooled to −10°. Over 10 minutes, 38 ml. of 2.4M n-butyllithium in hexane is added, and the mixture is stirred at from about −10° to about −15° for 15 minutes. The deep red suspension is cooled to −30° and a solution of 7.5 g (0.046 mole) of 4-acetyloxybenzaldehyde in 10 ml. of tetrahydrofuran is added dropwise. Towards the end of the addition the color is discharged. The mixture is allowed to warm to 20° overnight, whereupon TLC (silica, ether:hexane; 1:1) shows 3 major spots. The mixture is evaporated to dryness and then partitioned between water and ether. Carbon dioxide is passed through the mixture until the pH is about 8.0. The organic layer is separated, dried ($Na_2SO_4$) and evaporated onto 200 ml. of silica (60–200 mesh). This is loaded on an 800 ml. dry silica column and eluted with 10% ether in hexane. The least polar (#1) of the triad (#1–#3) is eluted cleanly, followed by pure #2, mixtures #2 and #3, and pure #3. Fractions containing #3 are evaporated to give 1.6 g. of 4-(2-methoxyethenyl)phenol as an oil which solidifies on cooling.

The remaining mixed fractions of #2 and #3 and the pure #2 are combined and the resulting oil is covered with 400 ml. of 2.5% sodium hydroxide under argon. After stirring for 24 hours, the oil is completely dissolved. The aqueous phase is extracted twice with ether and then treated with carbon dioxide until the pH is about 8.0. Extaction with ethyl acetate, drying ($Na_2SO_4$), and evaporation gives another 3.9 g. of 4-(2-methoxyethenyl)phenol as an oil which solidifies in the cold.

(b) (S)-1-[(S)-3-(Benzoylthio)-2-methyl-1-oxopropyl]-4-[4-(2-methoxyethenyl)phenoxy]-L-proline, diphenylmethyl ester A mixture of 5.03 g. (0.01 mole) of [1(S),4R]-1-[3-(benzoylthio)-2-methyl-1-oxopropyl]-4-hydroxy-L-proline, diphenylmethyl ester, 2.62 g. (0.01 mole) of triphenylphosphine and 1.5 g. (0.01 mole) of 4-(2-methoxyethenyl)phenol is taken up in benzene and evaporated to dryness. The residue is dissolved in 75 ml. of dry tetrahydrofuran, cooled to −10° under argon, and treated with 17.4 g. (0.01 mole) of diethylazodicarboxylate. The mixture is allowed to come to 20° over one hour, then heated to 60° for 5 hours, and cooled to 25° overnight. Evaporation gives a foam. This is taken up in benzene, filtered, and chromatographed on a 1 l. dry silica column (60–200 mesh) in hexane:acetone (4:1). The product containing fractions are pooled and evaporated to give 3.9 g. of (S)-1-[(S)-3-(benzoylthio)-2-methyl-1-oxopropyl]-4-[4-(2-methoxyethenyl)phenoxy]-L-proline, diphenylmethyl ester as a colorless tacky oil.

(c)

(S)-4-[4-[[7-(Aminosulfonyl)-6-chloro-3,4-dihydro-1,1-dioxo-2H-1,2,4-benzothiadiazin-3-yl]methyl]phenoxy]-1-[(S)-3-(benzoylthio)-2-methyl-1-oxopropyl]-L-proline The diphenylmethyl ester product from part (b) (3.8 g., 5.7 mmole) in 100 ml. of acetonitrile is added to a solution of 4-amino-6-chloro-1,3-benzenedisulfonamide prepared by dissolving 2.0 g. (7.0 mmoles) in 200 ml. of acetonitrile and distilling to 125 ml. The resulting mixture is treated with 1.5 ml. of anisole followed by 200 mg. of toluenesulfonic acid. The mixture is brought to reflux and concentrated to 150 ml. After one hour the mixture is evaporated to a foam, taken up in ethyl acetate, washed with water and brine, dried ($Na_2SO_4$) and evaporated. Trituration with ether gives an impure beige product; TLC (silica, ethyl acetate:pyridine:acetic acid:water; 300:20:6:11) $R_f=0.27$. This solid is taken up in 200 ml. of ethyl acetate and applied to 800 ml. dry silica (60-200 mesh) and eluted with ethyl acetate until the non-polar ($R_f$ greater than 0.6) material is eluted. Solvents are switched to ethyl acetate:pyridine:acetic acid:water (300:20:6:11), and the clean product fractions are pooled and evaporated. The resulting pyridine solution is diluted with water and filtered. The filter pad is washed with water and then extracted with ethyl acetate. The organics are dried ($Na_2SO_4$) and evaporated to a foam smelling slightly of pyridine. Cyclohexane is added and evaporated to give a pyridine free foam. Trituration with ether gives 2.0 g. of a cream colored solid with a slight polar contaminant. Chromatography on 200 g. of LH-20 in methanol gives a clean separation. Pooling and evaporating product fractions and trituration of the resulting glass with ether and drying at 25° in vacuo over $P_2O_5$ for 12 hours gives 1.6 g. of (S)-4-[4-[[7-(aminosulfonyl)-6-chloro-3,4-dihydro-1,1-dioxo-2H-1,2,4-benzothiadiazin-3-yl]methyl]phenoxy]-1-[(S)-3-(benzoylthio)-2-methyl-1-oxopropyl]-L-proline; m.p. 180°-185°; $[\alpha]_D=-24°$ (c=0.1%, methanol). TLC (silica gel, methylene chloride:methanol:acetic acid; 8:1:1) $R_f=0.40$.

Anal. calc'd. for $C_{30}H_{31}ClN_4O_9S_3$: C, 49.82; H, 4.32; N, 7.75; S, 13.30; Cl, 4.90. Found: C, 49.61; H, 4.72; N, 7.37; S, 12.99; Cl, 4.82.

EXAMPLE 2

(S)-4-[4-[[7-(Aminosulfonyl)-6-chloro-3,4-dihydro-1,1-dioxo-2H-1,2,4-benzothiadiazin-3-yl]methyl]phenoxy]-1-[(S)-3-mercapto-2-methyl-1-oxopropyl]-L-proline The product from Example 1 (0.3 g., 0.4 mmole) is dissolved in 50 ml. of argon purged sodium hydroxide (2.5%) and stirred at 25° for 3 hours. The solution is acidified with 10% potassium bisulfate and extracted with ethyl acetate. The organics are dried ($Na_2SO_4$) and evaporated. Trituration with ether gives a solid. Chromatography on 50 g. of LH-20 in methanol and pooling and evaporation of the product containing fractions gives a glass. Trituration with ether gives 0.2 g. of (S)-4-[[7-(aminosulfonyl)-6-chloro-3,4-dihydro-1,1-dioxo-2H-1,2,4-benzothiadiazin-3-yl]methyl]phenoxy]-1-[(S)-3-mercapto-2-methyl-1-oxopropyl]-L-proline as a white crystalline solid; m.p. 175°-185°; $[\alpha]_D=-22°$ (c=0.1%, methanol). TLC (silica, methylene chloride:methanol:acetic acid; 8:1:1) $R_f=0.32$.

Anal. calc'd. for $C_{23}H_{27}ClN_4O_8S_3$: C, 44.62; H, 4.40; N, 9.05; S, 15.54; Cl, 5.73; SH, 5.34. Found: C, 44.57; H, 4.62; N, 8.71; S, 15.30; Cl, 5.65; SH, 5.23.

EXAMPLE 3

(S)-4-[4-[[7-(Aminosulfonyl)-3,4-dihydro-1,1-dioxo-6-(trifluoromethyl)-2H-1,2,4-benzothiadiazin-3-yl]methyl]phenoxy]-1-[(S)-3-(benzoylthio)-2-methyl-1-oxopropyl]-L-proline To a mixture of (S)-1-[(S)-3-(benzoylthio)-2-methyl-1-oxopropyl]-4-[4-(2-methoxyethenyl)phenoxy]-L-proline, diphenylmethyl ester (3.6 g., 5.66 mmole), 4-amino-6-(trifluoromethyl)-1,3-benzenedisulfonamide (1.8 g., 5.7 mmole) and anisole (3.5 ml.) in 80 ml. of acetonitrile is added 120 mg. of p-toluenesulfonic acid. The reaction is essentially complete after refluxing for one hour. The solvent is removed under vacuum and the residue is triturated with diethyl ether to give a solid. The solid is purified by chromatography on an LPS-1 column eluted with ethyl acetate:pyridine:acetic acid:water (2400:50:15:27). After removal of the solvents on a rotary film evaporator using benzene to azeotrope off the acetic acid and pyridine, 3.8 g. of a homogeneous solid is obtained. Approximately half this material is passed through an LH-20 column (methanol) to give an analytically pure sample of (S)-4-[4-[[7-(aminosulfonyl)-3,4-dihydro-1,1-dioxo-6-(trifluoromethyl)-2H-1,2,4-benzothiadiazin-3-yl]methyl]phenoxy]-1-[(S)-3-(benzoylthio)-2-methyl-1-oxopropyl]-L-proline; m.p. 170°-182° (foams); $[\alpha]_D=-24.6°$ (c=1.0%, methanol). TLC (silica, methylene chloride:methanol:acetic acid; 8:1:1) $R_f=0.47$.

Anal. calc'd. for $C_{31}H_{31}F_3N_4O_9S_3$: C, 48.69; H, 4.20; N, 7.33; S, 12.58; F, 7.45. Found: C, 48.69; H, 4.20; N, 7.17; S, 12.51; F, 7.30.

EXAMPLE 4

(S)-4-[4-[[7-(Aminosulfonyl)-3,4-dihydro-1,1-dioxo-6-(trifluoromethyl)-2H-1,2,4-benzothiadiazin-3-yl]methyl]phenoxy]-1-[(S)-3-mercapto-2-methyl-1-oxopropyl]-L-proline The product of Example 3 (1.2 g., 1.62 mmole) is hydrolyzed under argon with 2.5% sodium hydroxide (150 ml.) for 1.75 hours at room temperature. The reaction solution is acidified with 10% potassium bisulfate and extracted with ethyl acetate. The organic phase is washed with water and brine and dried ($MgSO_4$). After evaporation to a glass and trituration with diethyl ether, 770 mg. of solid (S)-4-[4-[[7-(aminosulfonyl)-3,4-dihydro-1,1-dioxo-6-(trifluoromethyl)-2H-1,2,4-benzothiadiazin-3-yl]methyl]phenoxy]-1-[(S)-3-mercapto-2-methyl-1-oxopropyl]-L-proline is obtained; m.p. decomposition above 217°; $[\alpha]_D=-26.3°$ (c=1.0%, methanol). TLC (silica, ethyl acetate:pyridine:acetic acid:water; 240:20:6:11) $R_f=0.37$.

Anal. calc'd. for $C_{24}H_{27}F_3N_4O_8S_3$: C, 44.17; H, 4.17; N, 8.58; S, 14.74; F, 8.73; SH, 5.07. Found: C, 43.85; H, 4.32; N, 8.26; S, 14.61; F, 8.48; SH, 5.06.

EXAMPLE 5

(S)-4-[4-[[7-(Aminosulfonyl)-6-chloro-3,4-dihydro-2-methyl-1,1-dioxo-2H-1,2,4-benzothiadiazin-3-yl]methyl]phenoxy]-1-[(S)-3-(benzoylthio)-2-methyl-1-oxopropyl]-L-proline (a)

4-Amino-6-chloro-$N^3$-methyl-1,3-benzenedisulfonamide

A mixture of 4-amino-6-chloro-1,3-benzenedisulfonamide (30 g., 105 mmole) and urea (12.6 g., 210 mmole)

are ground together and then heated in a 200°–205° oil bath. Within 30 minutes the sample is a molten foam, which in another 30 minutes resolidifies. After a further 30 minutes heating, the flask is cooled and the contents slurried in water and acidified. The cream-colored powder is filtered, washed with water, and dried azeotropically with benzene to yield 31 g. of 6-chloro-3,4-dihydro-3-oxo-2H-1,2,4-benzothiadiazine-7-sulfonamide, 1,1-dioxide.

Under argon, this 6-chloro-3,4-dihydro-3-oxo-2H-1,2,4-benzothiadiazine-7-sulfonamide, 1,1-dioxide (10 g., 30 mmole) is dissolved in dimethylformamide (25 ml.) at 60°–65°. To this is added 1 equivalent of sodium hydride (60% in mineral oil, 1.24 g., 30 mmole) in portions. After heating and stirring for 15 minutes, methyl iodide (4.2 g., 30 mmole) is dripped in over 5 minutes. The mixture is then heated at 60°–65° for one hour. The mixture is cooled somewhat and added to cold water (800 ml.), giving beige crystals and a yellow aqueous solution. The solid is washed with water and air-dried to give 9.2 g. of 6-chloro-3,4-dihydro-2-methyl-3-oxo-2H-1,2,4-benzothiadiazepin-7-sulfonamide, 1,1-dioxide.

The above 6-chloro-3,4-dihydro-2-methyl-3-oxo-2H-1,2,4-benzothiadiazine-7-sulfonamide, 1,1-dioxide (9.2 g., 28 mmole) is dissolved in 20% sodium hydroxide (90 ml.) and refluxed overnight in a 120°–140° oil bath. The clear solution goes from brown to yellow. The mixture is diluted with water (350 ml.) and extracted with hexane. The aqueous phase is acidified with concentrated hydrochloric acid and chilled at 5° for 36 hours. The resulting beige solid is filtered, washed with water, and dried azeotropically with benzene to give 8.0 g. of crude product. Recrystallization of 6 g. of this material from ethanol (100 ml.) and water (200 ml.) gives 4 g. of 4-amino-6-chloro-$N^3$-methyl-1,3-benzenedisulfonamide as off-white crystals; m.p. 168°–170°. [Literature m.p. 168°–169°, JACS, Vol. 82, p. 1132 (1960)].

(b)

(S)-4-[4-[[7-(Aminosulfonyl)-6-chloro-3,4-dihydro-2-methyl-1,1-dioxo-2H-1,2,4-benzothiadiazin-3-yl]methyl]phenoxy]-1-[(S)-3-(benzoylthio)-2-methyl-1-oxopropyl]-L-proline A mixture of (S)-1-[(S)-3-(benzoylthio)-2-methyl-1-oxopropyl]-4-[4-(2-methoxyethenyl)phenoxy]-L-proline, diphenylmethyl ester (4.0 g., 6.3 mmole), 4-amino-6-chloro-$N^3$-methyl-1,3-benzenedisulfonamide (1.89 g., 1 eq.), 4 ml. anisole, and 130 mg. p-toluenesulfonic acid in 200 ml. of acetonitrile is refluxed. 80 ml. of acetonitrile is distilled off in order to azeotrope off water. The reaction appears to be complete as soon as the distillation is finished. The reaction solution is evaporated and the residue is triturated with diethyl ether. The solid is flash chromatographed on LPS-1 silica eluting with ethyl acetate:acetone (1:1) followed by 10% acetic acid:acetone. After concentrating to a residue, water is added and the gummy solid is absorbed on a filter pad and washed with water to remove acetic acid. The product is then washed from the pad with ethyl acetate. The ethyl acetate solution is washed with water, dried ($Na_2SO_4$), and concentrated to a residue (3 g.). A portion of this residue is run through an LH-20 (methanol) column to give an analytically pure sample of (S)-4-[4-[[7-(aminosulfonyl)-6-chloro-3,4-dihydro-2-methyl-1,1-dioxo-2H-1,2,4-benzothiadiazin-3-yl]methyl]phenoxy]-1-[(S)-3-(benzoylthio)-2-methyl-1-oxopropyl]-L-proline; m.p. 228° (decomposition); $[\alpha]_D = -31.7°$ (c=1.0%, methanol). TLC (silica, methylene chloride:methanol:acetic acid, 8:1:1) $R_f = 0.52$.

Anal. calc'd. for $C_{31}H_{33}ClN_4O_9S_3.0.29H_2O$: C, 50.14; H, 4.56; N, 7.55; S, 12.95; Cl, 4.77. Found: C, 50.14; H, 4.60; N, 7.35; S, 12.95; Cl, 4.76.

EXAMPLE 6

(S)-4-[4-[[7-(Aminosulfonyl)-6-chloro-3,4-dihydro-2-methyl-1,1-dioxo-2H-1,2,4-benzothiadiazin-3-yl]methyl]phenoxy]-1-[(S)-3-mercapto-2-methyl-1-oxopropyl]-L-proline To 50 ml. of 2.5% sodium hydroxide at 25° under argon purge is added 400 mg. (0.54 mmole) of the product of Example 5. After 1.5 hours at 25°, excess solid potassium bisulfate is added and the mixture is extracted with ethyl acetate. The extracts are washed with water, dried ($Na_2SO_4$), and evaporated to a yellow foam. This is triturated with ether to a powder that is chromatographed on 200 g. of Sephadex LH-20 in methanol. Pure major product fractions are combined and evaporated, and the resulting glass is triturated with ether to give 92 mg. of (S)-4-[4-[[7-(aminosulfonyl)-6-chloro-3,4-dihydro-2-methyl-1,1-dioxo-2H-1,2,4-benzothiadiazin-3-yl]methyl]phenoxy]-1-[(S)-3-mercapto-2-methyl-1-oxopropyl]-L-proline; m.p. 192°–197°; $[\alpha]_D = -43.8°$ (c=1.0%, methanol). TLC (silica, methylene chloride:methanol:acetic acid; 8:1:1) $R_f = 0.27$.

Anal. calc'd. for $C_{24}H_{29}ClN_4O_8S_3.1.25H_2O$: C, 43.96; H, 4.84; N, 8.54; S, 14.67; Cl, 5.41; SH, 5.04. Found: C, 43.95; H, 4.52; N, 8.19; S, 14.75; Cl, 5.46; SH, 5.13.

EXAMPLES 7-20

Following the procedure of Examples 1, 3 and 5, the substituted phenoxy or phenylthio proline diphenylmethyl ester of Col. I is reacted with the benzenamine of Col. II to yield, after removal of the ester group, the acylmercaptoalkanoyl product of Col. III. Treatment with base according to the procedure of Examples 2, 4 and 6 yields the mercaptoalkanoyl product of Col. IV.

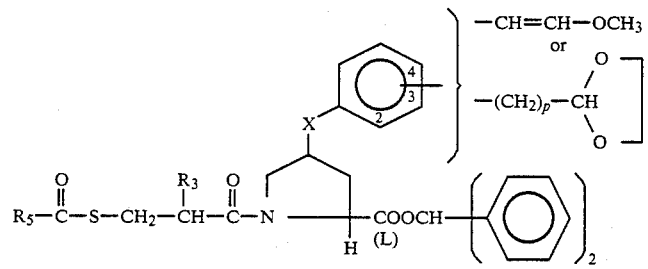

Col. I

-continued

Col. II

Col. III

Col. IV

| Example | $R_5$ | $R_3$ | X | position | p | $R_{14}$ | $R_a$ | $R_b$ | $R_c$ | $R_d$ | Z |
|---|---|---|---|---|---|---|---|---|---|---|---|
| 7 |  | —CH$_3$ | S | 4 | 1 | H | H | Cl | SO$_2$NH$_2$ | H | CO |
| 8 |  | —CH$_3$ | O | 4 | 1 | —CH$_3$ | H | Cl | SO$_2$NH$_2$ | H | CO |
| 9 |  | —CH$_3$ | S | 3 | 1 | H | H | Cl | SO$_2$NH$_2$ | H | SO$_2$ |
| 10 |  | —CH$_3$ | O | 2 | 1 | H | H | CF$_3$ | SO$_2$NH$_2$ | H | SO$_2$ |
| 11 |  | —CH$_3$ | S | 4 | 2 | H | H | Cl | SO$_2$NH$_2$ | H | SO$_2$ |
| 12 |  | —CH$_3$ | O | 4 | 3 | H | H | Cl | SO$_2$NH$_2$ | H | CO |
| 13 |  | —CH$_3$ | S | 4 | 4 | H | H | Cl | SO$_2$NH$_2$ | H | SO$_2$ |
| 14 | H$_3$C— | —CH$_3$ | S | 3 | 1 | —CH$_3$ | Cl | H | SO$_2$NH$_2$ | H | CO |
| 15 | H$_3$C— | H | O | 2 | 1 | H | H | OC$_2$H$_5$ | SO$_2$NH$_2$ | H | SO$_2$ |
| 16 |  | —CH$_3$ | S | 4 | 2 | H | H | NO$_2$ | SO$_2$NH$_2$ | H | CO |
| 17 | 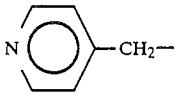 | —C$_2$H$_5$ | O | 2 | 3 | H | H | CF$_3$ | NO$_2$ | H | SO$_2$ |

| | | | | | | | | | | | |
|---|---|---|---|---|---|---|---|---|---|---|---|
| 18 | Cl—⟨phenyl⟩— | —CH₃ | S | 4 | 1 | H | H | Cl | NO₂ | H | CO |
| 19 | ⟨phenyl⟩—CH₂— | —CH₃ | O | 4 | 1 | —CH₃ | Cl | H | SO₂NH₂ | H | SO₂ |
| 20 | H₅C₂— | —CH₃ | S | 4 | 1 | H | H | Cl | SO₂NH₂ | H | SO₂ |

EXAMPLE 21

(cis)-4-[4-[[7-(Aminosulfonyl)-6-chloro-3,4-dihydro-1,1-dioxo-2H-1,2,4-benzothiadiazin-3-yl]methyl]phenoxy]-1-[[(3-ethoxy-3-oxopropyl)ethylamino]carbonyl]-L-proline

(a) 3-(Ethylamino)propanoic acid, ethyl ester

Into 200 ml. of cold (−60°) absolute ethanol is passed anhydrous ethylamine (36 g., 781 mmole, 1.1 eq.). To the resulting ethanolic solution is added dropwise a solution of ethyl acrylate (71 g., 710 mmole, 1 eq.) in 150 ml. of absolute ethanol over a period of several hours. The resulting mixture is then stirred at −60° for 0.5 hours and allowed to warm slowly to room temperature where it is stirred for another 20 hours. The solvent is removed at reduced pressure to give 33 g. of 3-(ethylamino)propanoic acid, ethyl ester as colorless liquid; b.p. 80°–83°.

(b) (trans)-1-[[(3-Ethoxy-3-oxopropyl)ethylamino]carbonyl]-4-hydroxy-L-proline, phenylmethyl ester To a cold (−30°) solution of 1.25M phosgene in benzene (25.52 ml., 1.5 eq.) in 20 ml. of anhydrous dichloromethane under argon is added dropwise a solution of 3-(ethylamino)propanoic acid, ethyl ester (3.09 g., 21.26 mmole) and N-methylmorpholine (3.5 ml., 1.5 eq.) in 20 ml. of dichloromethane. The resulting mixture is stirred for one hour at −30° and then for one hour at room temperature. The solvent is removed at reduced pressure. Additional dichloromethane is added and the solution is concentrated once more.

This residue is dissolved in 30 ml. of dichloromethane and (trans)-4-hydroxy-L-proline, phenylmethyl ester, hydrochloride (6.9 g., 1.2 eq.) is added. To the resulting suspension is added dropwise N-methylmorpholine (5.6 ml., 2.4 eq.) in 20 ml. of dichloromethane. The resulting mixture is stirred at room temperature for 15 hours. The solvent is removed at reduced pressure and the residue taken up in ethyl acetate. This is washed with water (twice), 1N hydrochloric acid (twice), 1N sodium bicarbonate (twice), and once with brine. After drying (MgSO₄), the solvent is removed at reduced pressure. The residue is flash chromatographed (Whatman silica gel LPS-1, hexane:ethyl acetate; 65:35) to give 7.72 g. of (trans)-1-[[(3-ethoxy-3-oxopropyl)ethylamino]carbonyl]-4-hydroxy-L-proline, phenylmethyl ester as a colorless oil; TLC (silica gel, ethyl acetate) $R_f=0.34$.

(c) (cis)-4-[4-(2-Methoxyethenyl)phenoxy]-1-[[(3-ethoxy-3-oxopropyl)ethylamino]carbonyl]-L-proline, phenylmethyl ester Equimolar amounts of (trans)-1-[[(3-ethoxy-3-oxopropyl)ethylamino]carbonyl]-4-hydroxy-L-proline, phenylmethyl ester and 4-(2-methoxyethenyl)phenol are reacted in the presence of triphenylphosphine and diethylazodicarboxylate to give (cis)-4-[4-(2-methoxyethenyl)phenoxy]-1-[[(3-ethoxy-3-oxopropyl)ethylamino]carbonyl]-L-proline, phenylmethyl ester.

(d) (cis)-4-[4-[[7-(Aminosulfonyl)-6-chloro-3,4-dihydro-1,1-dioxo-2H-1,2,4-benzothiadiazin-3-yl]methyl]phenoxy]-1-[[(3-ethoxy-3-oxopropyl)ethylamino]carbonyl]-L-proline, phenylmethyl ester.

The diphenylmethyl ester product from part (c) in acetonitrile is reacted with a solution of 4-amino-6-chloro-1,3-benzenedisulfonamide in acetonitrile according to the procedure of 1(c) to give (cis)-4-[[7-(aminosulfonyl)-6-chloro-3,4-dihydro-1,1-dioxo-2H-1,2,4-benzothiadiazin-3-yl]methyl]phenoxy]-1-[[(3-ethoxy-3-oxopropyl)ethylamino]carbonyl]-L-proline, phenylmethyl ester.

(e) (cis)-4-[4-[[7-(Aminosulfonyl)-6-chloro-3,4-dihydro-1,1-dioxo-2H-1,2,4-benzothiadiazin-3-yl]methyl]phenoxy]-1-[[(3-ethoxy-3-oxopropyl)ethylamino]carbonyl]-L-proline A solution of the phenylmethyl ester product from part (d) in absolute ethanol is treated with 10% palladium on charcoal. The resulting mixture is stirred under hydrogen for several hours. The mixture is filtered and concentrated under reduced pressure to give (cis)-4-[[[7-(aminosulfonyl)-6-chloro-3,4-dihydro-1,1-dioxo-2H-1,2,4-benzothiadiazin-3-yl]methyl]phenoxy]-1-[[(3-ethoxy-3-oxopropyl)ethylamino]carbonyl]-L-proline.

EXAMPLE 22

(cis)-4-[4-[[7-(Aminosulfonyl)-6-chloro-3,4-dihydro-1,1-dioxo-2H-1,2,4-benzothiadiazin-3-yl]methyl]phenoxy]-1-[[(2-carboxyethyl)ethylamino]carbonyl]-L-proline The product from Example 21 is dissolved in aqueous tetrahydrofuran and treated with a molar excess of aqueous sodium hydroxide. After the reaction is completed, the solution is acidified with dilute hydrochloric acid to precipitate out (cis)-4-[4-[[7-(aminosulfonyl)-6-chloro-3,4-dihydro-1,1-dioxo-2H-1,2,4-benzothiadiazin-3-yl]methyl]phenoxy]-1-[[(2-carboxyethyl)ethylamino]carbonyl]-L-proline.

EXAMPLES 23–31

Following the procedure of Example 21 but employing the substituted phenoxy or phenylthio proline ester shown in Col. I and the substituted benzenamine shown in Col. II one obtains the L-proline ester product shown in Col. III which is then hydrogenated to the product shown in Col. IV.

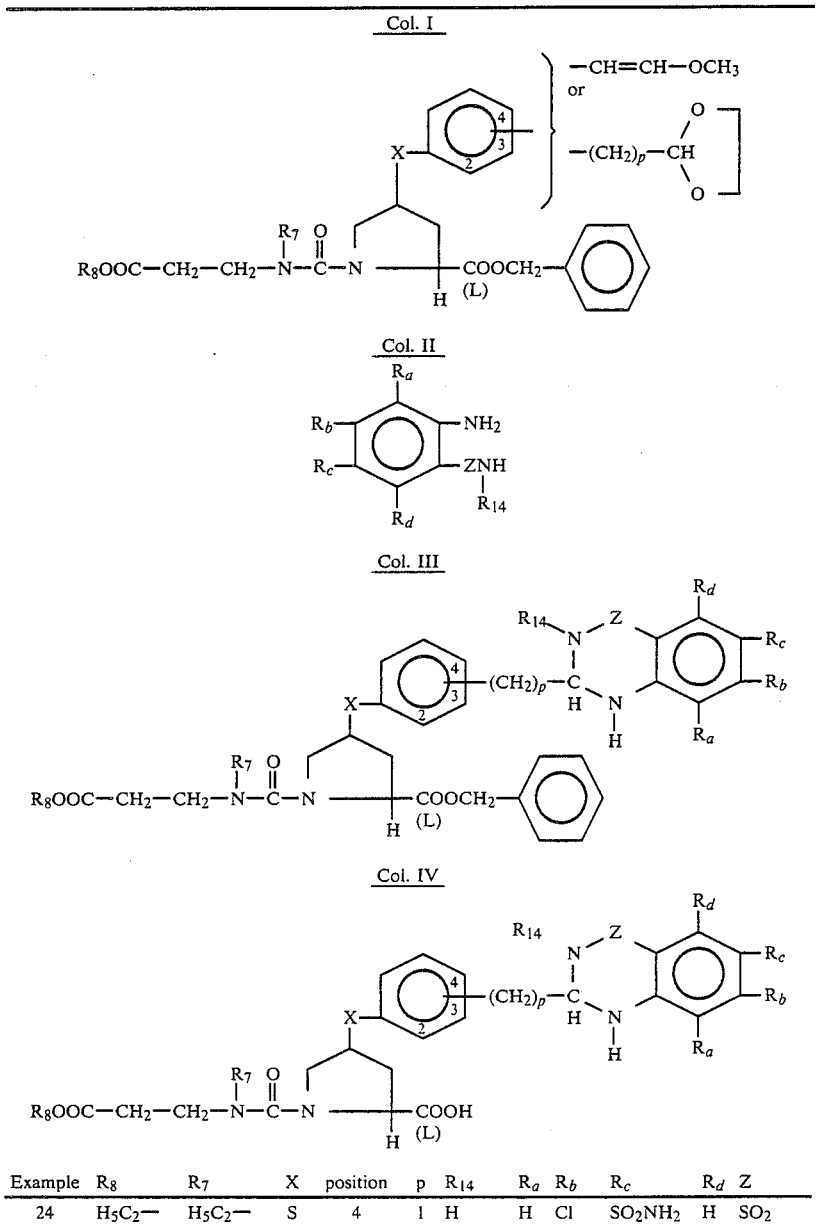

EXAMPLE 32

(cis)-4-[4-[[7-(Aminosulfonyl)-6-chloro-3,4-dihydro-1,1-dioxo-2H-1,2,4-benzothiadiazin-3-yl]methyl]phenoxy]-1-[[hydroxy(4-phenylbutyl)phosphinyl]acetyl]-L-proline, disodium salt (a) 1-[(2,2-Dimethylethoxy)carbonyl]-(cis)-4-[4-(2-methoxyethenyl)phenoxy]-L-proline, diphenylmethyl ester A mixture of 1-[(2,2-dimethylethoxy)carbonyl]-(trans)-4-hydroxy-L-proline, diphenylmethyl ester, triphenylphosphine, and 4-(2-methoxyethenyl)phenol is taken up in benzene and evaporated to dryness. The residue is dissolved in dry tetrahydrofuran, cooled to −10° under argon, and treated with diethylazodicarboxylate. The reaction mixture is worked up according to the procedure of Example 1(b) to yield 1-[(2,2-dimethylethoxy)carbonyl]-(cis)-4-[4-(2-methoxyethenyl)-phenoxy]-L-proline, diphenylmethyl ester.

(b)
(cis)-4-[4-[[7-(Aminosulfonyl)-6-chloro-3,4-dihydro-1,1-dioxo-2H-1,2,4-benzothiadiazin-3-yl]methyl]phenoxy]-L-proline, trifluoroacetate salt The diphenylmethyl ester product from part (a) in acetonitrile is added to a solution of 4-amino-6-chloro-1,3-benzenedisulfonamide in acetonitrile according to the procedure of Example 1(c). The resulting mixture is treated with 1.5 ml. of anisole followed by 200 mg. of toluenesulfonic acid and the reaction mixture is worked up according to the procedure of Example 1(c) to give (cis)-4-[4-[[7-(aminosulfonyl)-6-chloro-3,4-dihydro-1,1-dioxo-2H-1,2,4-benzothiadiazin-3-yl]methyl]phenoxy]-L-proline, trifluoroacetate salt.

(c)
(cis)-4-[4-[[7-(Aminosulfonyl)-6-chloro-3,4-dihydro-1,1-dioxo-2H-1,2,4-benzothiadiazin-3-yl]methyl]phenoxy]-1-[[hydroxy(4-phenylbutyl)phosphinyl]acetyl]-L-proline, disodium salt

[Ethoxy(4-phenylbutyl)phosphinyl]acetic acid is dissolved in dry tetrahydrofuran and N,N'-carbonyldiimidazole is added. This reaction mixture is stirred at room temperature for several hours. The (cis)-4-[4-[[7-(aminosulfonyl)-6-chloro-3,4-dihydro-1,1-dioxo-2H-1,2,4-benzothiadiazin-3-yl]methyl]phenoxy]-L-proline, trifluoroacetate salt from part (b) in tetrahydrofuran is added to the reaction mixture. Triethylamine is then added and the resulting mixture is stirred under argon at room temperature overnight.

The reaction mixture is then dissolved in a mixture of ethyl acetate and 10% potassium bisulfate and the phases separated. After washing with brine and drying (MgSO$_4$), the ethyl acetate is evaporated. The ethyl ester product is hydrolyzed in a solution of 1N sodium hydroxide for about 30 minutes. The aqueous solution of product is adjusted to pH of about 8.0 and run through an HP-20 column eluting with an acetonitrile/water gradient. The product containing fractions are lyophilized to give (cis)-4-[4-[[7-(aminosulfonyl)-6-chloro-3,4-dihydro-1,1-dioxo-2H-1,2,4-benzothiadiazin-3-yl]methyl]phenoxy]-1-[[hydroxy(4-phenylbutyl)phosphinyl]acetyl]-L-proline, disodium salt.

EXAMPLES 33–45

Following the procedure of Example 32 the N-protected-4-substituted-L-proline, diphenylmethyl ester shown in Col. I is reacted with the benzenamine of Col. II to yield, after removal of the ester group and the N-protecting group, the 4-substituted-L-proline shown in Col. III. This intermediate is then reacted with the phosphinylacetic acid ester shown in Col. IV to yield the product shown in Col. V. In Examples 33 to 42 the R$_{13}$ ester group can be removed by hydrolysis to yield the corresponding diacid which can then be converted to a disalt.

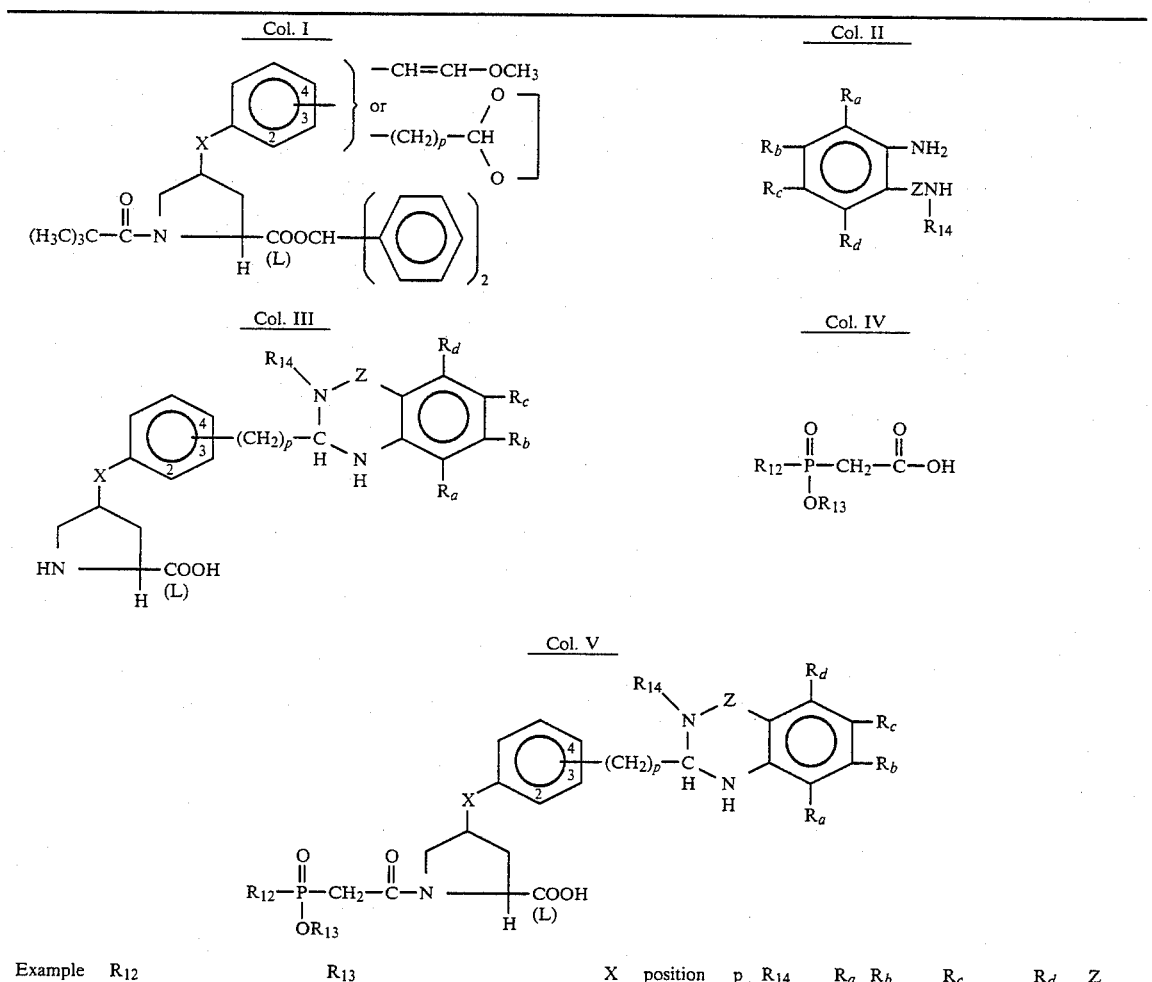

| Example | R$_{12}$ | R$_{13}$ | X | position | p | R$_{14}$ | R$_a$ | R$_b$ | R$_c$ | R$_d$ | Z |
|---|---|---|---|---|---|---|---|---|---|---|---|

-continued

| # | R group | R' | X | a | b | c | d | e | f | g | Z |
|---|---|---|---|---|---|---|---|---|---|---|---|
| 33 | phenyl-(CH₂)₄– | –C₂H₅ | S | 4 | 1 | H | H | Cl | SO₂NH₂ | H | CO |
| 34 | phenyl-(CH₂)₃– | –C₂H₅ | O | 4 | 1 | –CH₃ | H | Cl | SO₂NH₂ | H | CO |
| 35 | H₃C–(H₂C)₅– | –C₂H₅ | O | 3 | 1 | H | H | Cl | SO₂NH₂ | H | SO₂ |
| 36 | pyridyl-(CH₂)₄– | –C₂H₅ | O | 2 | 1 | H | H | CF₃ | SO₂NH₂ | H | SO₂ |
| 37 | cyclohexyl-(CH₂)₂– | –C₂H₅ | S | 4 | 2 | H | H | OC₂H₅ | SO₂NH₂ | H | SO₂ |
| 38 | phenyl– | –C₂H₅ | O | 4 | 3 | H | H | Cl | SO₂NH₂ | H | CO |
| 39 | thienyl-CH₂– | –C₂H₅ | O | 4 | 1 | –CH₃ | Cl | H | SO₂NH₂ | H | SO₂ |
| 40 | phenyl-(CH₂)₆– | –C₂H₅ | S | 4 | 1 | H | H | Cl | SO₂NH₂ | H | SO₂ |
| 41 | phenyl-(CH₂)₄– | –C₂H₅ | S | 4 | 4 | H | H | NO₂ | SO₂NH₂ | H | SO₂ |
| 42 | phenyl-(CH₂)₃– | –C₂H₅ | S | 3 | 1 | –CH₃ | Cl | H | SO₂NH₂ | H | CO |
| 43 | phenyl-(CH₂)₂– | –CH(CH(CH₃)₂)–O–C(O)–C₂H₅ | O | 4 | 1 | H | H | Cl | SO₂NH₂ | H | SO₂ |
| 44 | phenyl-(CH₂)₄– | –CH(cyclohexyl)–O–C(O)–C₂H₅ | S | 4 | 2 | H | H | Cl | SO₂NH₂ | H | CO |
| 45 | phenyl-(CH₂)₄– | –CH₂–O–C(O)–phenyl | O | 4 | 1 | H | H | Cl | SO₂NH₂ | H | SO₂ |

EXAMPLE 46

(cis)-4-[4-[[7-(Aminosulfonyl)-6-chloro-3,4-dihydro-1,1-dioxo-2H-1,2,4-benzothiadiazin-3-yl]methyl]phenoxy]-1-[N-[(S)-1-carboxy-3-phenylpropyl]-L-alanyl]-L-proline, monosodium salt (a)

(cis)-4-[4-[[7-(Aminosulfonyl)-6-chloro-3,4-dihydro-1,1-dioxo-2H-1,2,4-benzothiadiazin-3-yl]methyl]phenoxy]-L-proline, methyl ester, hydrochloride Acetyl chloride is added to cold methanol (−20°) under argon. After stirring at −20° for 3 hours, (cis)-4-[4-[[7-(aminosulfonyl)-6-chloro-3,4-dihydro-1,1-dioxo-1,2,4-benzothiadiazin-3-yl]methyl]phenoxy]-L-proline, trifluoroacetate salt is added followed by the dropwise addition of thionyl chloride. After stirring for several hours at −20°, the cold bath is removed and the mixture is stirred at room temperature overnight. The solvent is removed at reduced pressure and the residue is treated with excess methanolic hydrochloric acid and then concentrated at reduced pressure to give (cis)-4-[4-[[7-(aminosulfonyl)-6-chloro-3,4-dihydro-1,1-dioxo-2H-1,2,4-benzothiadiazin-3-yl]methyl]phenoxy]-L-proline, methyl ester, hydrochloride.

(b)

(cis)-4-[4-[[7-(Aminosulfonyl)-6-chloro-3,4-dihydro-1,1-dioxo-2H-1,2,4-benzothiadiazin-3-yl]methyl]phenoxy]-1-[N-[(S)-1-ethoxycarbonyl-3-phenylpropyl]-L-alanyl]-L-proline, methyl ester Diphenylphosphoryl azide is added dropwise to a cold (°) solution of N-[1(S)-ethoxycarbonyl-3-phenylpropyl]-L-alanine and (cis)-4-[4-[[7-aminosulfonyl-6-chloro-3,4-dihydro-1,1-dioxo-2H-1,2,4-benzothiadiazin-3-yl]methyl]phenoxy]-L-proline, methyl ester, hydrochloride in dimethylformamide under argon. After stirring for several minutes, a solution of triethylamine in dimethylformamide is added dropwise over 10 minutes. After stirring for several hours, the cold bath is removed and the mixture is stirred overnight at room temperature. Work up of the reaction mixture and chromatographic separation yields (cis)-4-[[7-(aminosulfonyl)-6-chloro-3,4-dihydro-1,1-dioxo-2H-1,2,4-benzothiadiazin-3-yl]methyl]phenoxy[1-[N-(S)-1-ethoxycarbonyl-3-phenylpropyl]-L-alanyl]-L-proline, methyl ester.

(c)

(cis)-4-[4-[[7-(Aminosulfonyl)-6-chloro-3,4-dihydro-1,1-dioxo-2H-1,3,4-benzothiadiazin-3-yl]methyl]phenoxy]-1-[N-[(S)-1-carboxy-3-phenylpropyl]-L-alanyl]-L-proline, monosodium salt 1N Sodium hydroxide is added to a solution under argon of the methyl ester product from part(b) in ethanol. After stirring at room temperature for several hours, the aqueous solution is adjusted to a pH of about 8.0 and run through an HP-20 column eluting with an acetonitrile/water gradient. The product containing fractions are lyophilized to give (cis)-4-[4-[[7-(aminosulfonyl)-6-chloro-3,4-dihydro-1,1-dioxo-2H-1,2,4-benzothiadiazin-3-yl]methyl]phenoxy]-1-[N-[(S)-1-carboxy-3-phenylpropyl]-L-alanyl]-L-proline, monosodium salt.

Similarly, by employing the 4-substituted-L-proline shown in Col. III of Examples 33–45 within the above procedure, other compounds within the scope of the invention are obtained.

EXAMPLE 47

1000 tablets each containing the following ingredients:

| | |
|---|---|
| (S)-4-[4-[[7-(Aminosulfonyl)-6-chloro-3,4-dihydro-1,1-dioxo-2H—1,2,4-benzothiadiazin-3-yl]methyl]phenoxy]-1-[(S)—3-(benzoylthio)-2-methyl-1-oxopropyl]-L-proline | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S)-4-[4-[[7-(aminosulfonyl)-6-chloro-3,4-dehydro-1,1-dioxo-2H-1,2,4-benzothiadiazin-3-yl]methyl]phenoxy]-1-[(S)-3-(benzoylthio)-2-methyl-1-oxopropyl]-L-proline and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 46 can be prepared.

EXAMPLE 48

Two-piece #1 gelatin capsules each containing 100 mg. (S)-4-[4-[[7-(aminosulfonyl)-6-chloro-3,4-dihydro-1,1-dioxo-2H-1,2,4-benzothiadiazin-3-yl]methyl]phenoxy]-1-[(S)-3-mercapto-2-methyl-1-oxopropyl]-L-proline are filled with a mixture of the following ingredients:

| | |
|---|---|
| (S)-4-[4-[[7-(Aminosulfonyl)-6-chloro-3,4-dihydro-1,1-dioxo-2H—1,2,4-benzothiadiazin-3-yl]methyl]phenoxy]-1-[(S)-3-mercapto-2-methyl-1-oxopropyl]-L-proline | 100 mg. |
| Magnesium stearate | 7 mg. |
| Lactose | 193 mg. |
| | 300 mg. |

In a similar manner, capsules containing 100 mg. of the product of any of Examples 1 and 3 to 46 can be prepared.

EXAMPLE 49

An injectable solution is prepared as follows:

| | |
|---|---|
| (S)-4-[4-[[7-(Aminosulfonyl)-3,4-dihydro-1,1-dioxo-6-(trifluoromethyl)-2H—1,2,4-benzothiadiazin-3-yl]methyl]phenoxy]-1-[(S)-3-(benzoylthio)-2-methyl-1-oxopropyl]-L-proline | 500 g. |
| Methyl paraben | 5 g. |
| Propyl paraben | 1 g. |
| Sodium chloride | 25 g. |
| Water for injection | 5 l. |

The active substances, preservatives, and sodium chloride are dissolved in 3 liters of water for injection and then the volume is brought up to 5 liters. The solution is filtered through a sterile filter and aseptically filled into presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1,2, and 4 to 46.

What is claimed is:

1. A compound of the formula

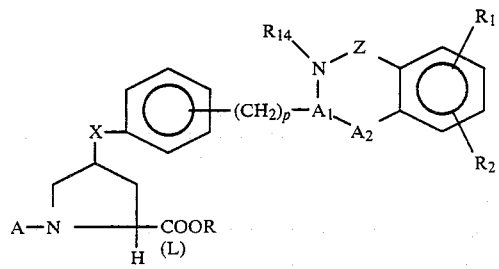

and a pharmaceutically acceptable salt thereof wherein
X is oxygen or sulfur;
—$A_1$-$A_2$— is —CH—NH— or —C=N—;
A is

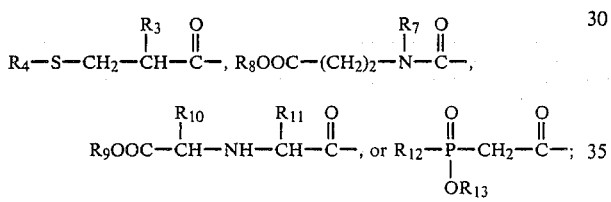

p is one, two, three or four;
R, $R_8$ and $R_9$ are independently selected from the group consisting of hydrogen, lower alkyl, benzyl, benzhydryl, and salt forming ion;
$R_1$ and $R_2$ are independently selected from the group consisting of hydrogen, halogen, lower alkyl, lower alkoxy, halo substituted lower alkyl, nitro, and —$SO_2NH_2$;
Z is

$R_3$ is hydrogen, lower alkyl, halo substituted lower alkyl, phenyl, benzyl, phenethyl or cycloalkyl;
$R_4$ is hydrogen or

$R_5$ is lower alkyl,

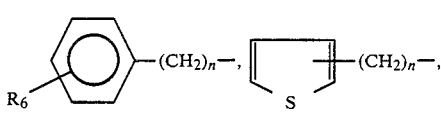

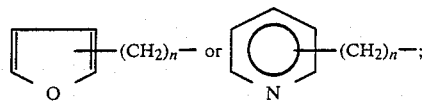

n is zero, one, two, three or four;
$R_6$ is hydrogen, lower alkyl, lower alkoxy, halogen, or hydroxy;
$R_7$ is lower alkyl or cycloalkyl;
$R_{10}$ is hydrogen, lower alkyl,

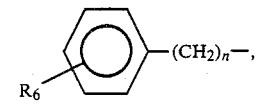

halo substituted lower alkyl, hydroxy substituted lower alkyl, —$(CH_2)_q$-cycloalkyl, —$(CH_2)_q$-N(lower alkyl)$_2$, —$(CH_2)_q$—$NH_2$, —$(CH_2)_q$-carboxy, —$(CH_2)_q$—SH, —$(CH_2)_q$-S-lower alkyl,

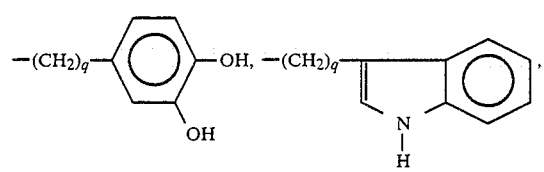

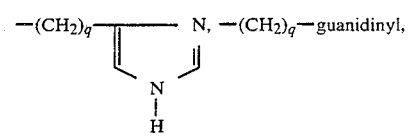

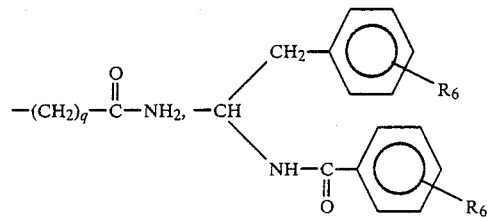

q is one, two, three or four;
$R_{11}$ is hydrogen, lower alkyl, halo substituted lower alkyl, hydroxy substituted lower alkyl, —$(CH_2)_q$—$NH_2$, —$(CH_2)_q$-N(lower alkyl)$_2$, —$(CH_2)_q$-quanidinyl,

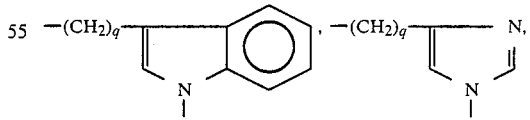

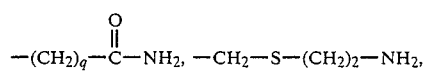

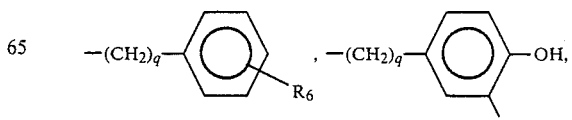

-continued

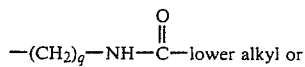

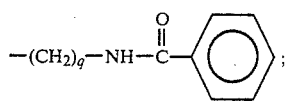

$R_{12}$ is alkyl of 1 to 10 carbons,

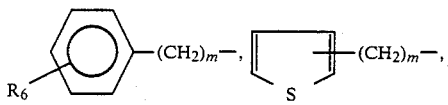

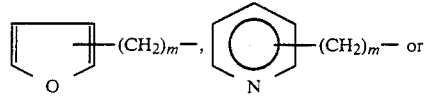

cycloalkyl—$(CH_2)_m$—;
m is zero or an integer from 1 to 7;
$R_{13}$ is hydrogen, lower alkyl, benzyl, benzhydryl, salt forming ion or

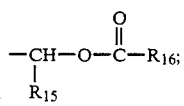

$R_{15}$ is hydrogen, lower alkyl, cycloalkyl or phenyl;
$R_{16}$ is hydrogen, lower alkyl, lower alkoxy, cycloalkyl, phenyl, benzyl, or phenethyl; and
$R_{14}$ is hydrogen, lower alkyl, cycloalkyl-$(CH_2)_n$—,

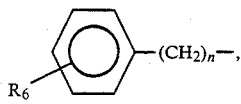

halo substituted lower alkyl, hydroxy substituted lower alkyl, —$(CH_2)_q$—N(lower alkyl)$_2$, or —$(CH_2)_q$—NH$_2$.

2. A compound of claim 1 of the formula

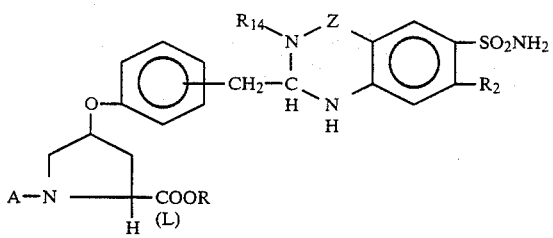

and a pharmaceutically acceptable salt thereof
wherein
R is hydrogen, lower alkyl of 1 to 4 carbons, or an alkali metal salt ion;
$R_{14}$ is hydrogen or lower alkyl of 1 to 4 carbons;
$R_2$ is halogen, lower alkyl of 1 to 4 carbons, or halo substituted lower alkyl of 1 to 4 carbons;
$R_4$ is hydrogen or

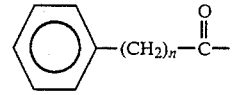

wherein n is zero, one or two;
$R_3$ is lower alkyl of 1 to 4 carbons;
$R_8$ is hydrogen, lower alkyl of 1 to 4 carbons, or an alkali metal salt ion;
$R_7$ is lower alkyl of 1 to 4 carbons;
$R_9$ is hydrogen, lower alkyl of 1 to 4 carbons, or an alkali metal salt ion;
$R_{10}$ is

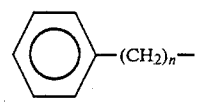

wherein n is zero, one, two, three or four;
$R_{11}$ is lower alkyl of 1 to 4 carbons, —$CH_2$—S—$(CH_2)_2$—$NH_2$, or —$(CH_2)_4$—$NH_2$;
$R_{12}$ is alkyl of 1 to 10 carbons or

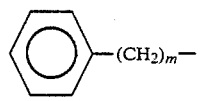

wherein m is zero or an integer from 1 to 7;
$R_{13}$ is hydrogen, alkali metal salt ion or

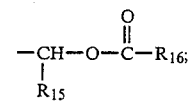

$R_{15}$ is hydrogen, straight or branched chain lower alkyl of 1 to 4 carbons, or cyclohexyl; and
$R_{16}$ is straight or branched chain lower alkyl of 1 to 4 carbons.

3. A compound of claim 2 wherein

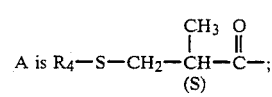

$R_{14}$ is hydrogen or methyl;
$R_2$ is chloro or trifluoromethyl;
$R_4$ is hydrogen or

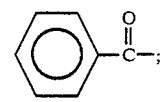

and
R is hydrogen or an alkali metal salt ion.

4. A compound of claim 3 wherein
$R_4$ is

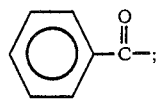

$R_{14}$ is hydrogen;
$R_2$ is chloro; and
R is hydrogen.

5. The compound of claim 4, (S)-4-[4-[[7-(aminosulfonyl)-6-chloro-3,4-dihydro-1,1-dioxo-2H-1,2,4-benzothiadiazin-3-yl]methyl]phenoxy]-1-[(S)-3-(benzoylthio)-2-methyl-1-oxopropyl]-L-proline.

6. A compound of claim 3 wherein
$R_4$ is hydrogen;
$R_{14}$ is hydrogen;
$R_2$ is chloro; and
R is hydrogen.

7. The compound of claim 6, (S)-4-[4-[[7-(aminosulfonyl)-6-chloro-3,4-dihydro-1,1-dioxo-2H-1,2,4-benzothiadiazin-3-yl]methyl]phenoxy]-1-[(S)-3-mercapto-2-methyl-1-oxopropyl]-L-proline.

8. A compound of claim 3
wherein
$R_4$ is

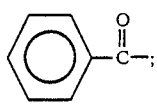

$R_{14}$ is hydrogen;
$R_2$ is trifluoromethyl; and
R is hydrogen.

9. The compound of claim 8, (S)-4-[4-[[7-(aminosulfonyl)-3,4-dihydro-1,1-dioxo-6-(trifluoromethyl)-2H-1,2,4-benzothiadiazin-3-yl]methyl]phenoxy]-1-[(S)-3-(benzoylthio)-2-methyl-1-oxopropyl]-L-proline.

10. A compound of claim 3 wherein
$R_4$ is hydrogen;
$R_{14}$ is hydrogen;
$R_2$ is trifluoromethyl; and
R is hydrogen.

11. The compound of claim 10, (S)-4-[4-[[7-(aminosulfonyl)-3,4-dihydro-1,1-dioxo-6-(trifluoromethyl)-2H-1,2,4-benzothiadiazin-3-yl]methyl]phenoxy]-1-[(S)-3-mercapto-2-methyl-1-oxopropyl]-L-proline.

12. A compound of claim 3
wherein
$R_4$ is

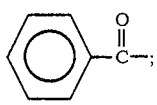

$R_{14}$ is methyl;
$R_2$ is chloro; and
R is hydrogen.

13. The compound of claim 12, (S)-4-[4-[[7-(aminosulfonyl)-6-chloro-3,4-dihydro-2-methyl-1,1-dioxo-2H-1,2,4-benzothiadiazin-3-yl]methyl]phenoxy]-1-[(S)-3-(benzoylthio)-2-methyl-1-oxopropyl]-L-proline.

14. A compound of claim 3
wherein
$R_4$ is hydrogen;
$R_{14}$ is methyl;
$R_2$ is chloro; and
R is hydrogen.

15. The compound of claim 14, (S)-4-[4-[[7-(aminosulfonyl)-6-chloro-3,4-dihydro-2-methyl-1,1-dioxo-2H-1,2,4-benzothiadiazin-3-yl]methyl]phenoxy]-1-[(S)-3-mercapto-2-methyl-1-oxopropyl]-L-proline.

16. A compound of claim 2
wherein
A is

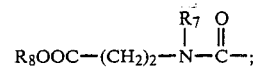

$R_8$ is hydrogen, ethyl, or an alkali metal salt ion;
$R_7$ is ethyl;
$R_{14}$ is hydrogen or methyl;
$R_2$ is chloro or trifluoromethyl; and
R is hydrogen or an alkali metal salt ion.

17. A compound of claim 2
wherein
A is

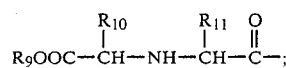

$R_9$ is hydrogen, ethyl, or an alkali metal salt ion;
$R_{10}$ is

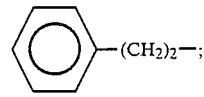

$R_{11}$ is methyl;
$R_{14}$ is hydrogen or methyl;
$R_2$ is chloro or trifluoromethyl; and
R is hydrogen or an alkali metal salt ion.

18. A compound of claim 2
wherein
A is

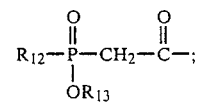

$R_{12}$ is

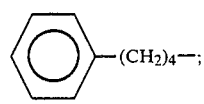

$R_{13}$ is hydrogen, alkali metal salt ion, or

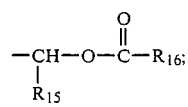

$R_{15}$ is hydrogen, straight or branched chain lower alkyl of 1 to 4 carbons, or cyclohexyl;
$R_{16}$ is straight or branched chain lower alkyl of 1 to 4 carbons;

$R_{14}$ is hydrogen or methyl;

$R_2$ is chloro or trifluoromethyl; and

R is hydrogen or an alkali metal salt ion.

19. A composition useful for treating hypertension comprising a pharmaceutically acceptable carrier and an effective amount of a hypotensive agent or pharmaceutically acceptable salt thereof of the formula

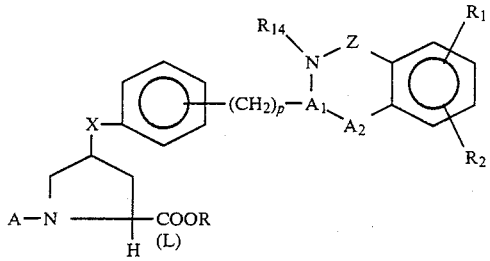

wherein A, —$A_1$-$A_2$—, R, $R_1$, $R_2$, $R_{14}$, p, X, and Z are as defined in claim 1.

20. The method of treating hypertension in a mammalian specie which comprises administering an effective amount of the composition of claim 19.

21. A compound of the formula

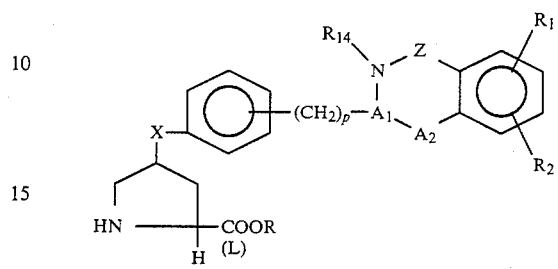

wherein —$A_1$-$A_2$—, p, R, $R_1$, $R_2$, $R_{14}$, X and Z are as defined in claim 1.

* * * * *